(12) United States Patent
Quan et al.

(10) Patent No.: US 11,744,783 B2
(45) Date of Patent: *Sep. 5, 2023

(54) NANOEMULSIONS COMPRISING FATTY ACID AND N-ACYL DERIVATIVES OF AMINO ACID SALT

(71) Applicant: Conopco, Inc., Englewood Cliffs, NJ (US)

(72) Inventors: Congling Quan, Woodbridge, CT (US); David John Lang, Southbury, CT (US)

(73) Assignee: CONOPCO, INC., Englewood Cliffs, NJ (US)

( * ) Notice: Subject to any disclaimer, the term of this patent is extended or adjusted under 35 U.S.C. 154(b) by 797 days.

This patent is subject to a terminal disclaimer.

(21) Appl. No.: 16/094,074

(22) PCT Filed: Apr. 4, 2017

(86) PCT No.: PCT/EP2017/057976
§ 371 (c)(1),
(2) Date: Oct. 16, 2018

(87) PCT Pub. No.: WO2017/182264
PCT Pub. Date: Oct. 26, 2017

(65) Prior Publication Data
US 2021/0220236 A1    Jul. 22, 2021

(30) Foreign Application Priority Data

Apr. 21, 2016    (EP) .................................... 16166487

(51) Int. Cl.
| A61K 8/06 | (2006.01) |
| A61K 8/31 | (2006.01) |
| A61K 8/44 | (2006.01) |
| A61K 8/36 | (2006.01) |
| A61Q 19/10 | (2006.01) |

(52) U.S. Cl.
CPC ................ *A61K 8/068* (2013.01); *A61K 8/31* (2013.01); *A61K 8/361* (2013.01); *A61K 8/44* (2013.01); *A61Q 19/10* (2013.01); *A61K 2800/21* (2013.01)

(58) Field of Classification Search
CPC ...... A61K 2800/21; A61K 8/31; A61K 8/062; A61K 8/922; A61K 8/068; A61K 8/361; A61K 8/44; A61Q 19/10
See application file for complete search history.

(56) References Cited

U.S. PATENT DOCUMENTS

| 5,500,152 | A | 3/1996 | Helliwell |
| 5,584,293 | A | 12/1996 | Darrow et al. |
| 6,066,608 | A | 5/2000 | Glenn, Jr. |
| 6,488,780 | B2 | 12/2002 | Cauwet-Martin |
| 6,541,018 | B1 | 4/2003 | Simonnet et al. |
| 8,357,381 | B2 | 1/2013 | Eskuchen et al. |
| 8,772,212 | B2 | 7/2014 | Restrepo et al. |
| 8,834,903 | B2 | 9/2014 | Simonnet et al. |
| 9,132,292 | B2 | 9/2015 | Allef et al. |
| 2002/0054861 | A1 | 5/2002 | Schmucker et al. |
| 2003/0012759 | A1* | 1/2003 | Bowen-Leaver ...... A61K 8/585 424/70.12 |
| 2003/0077299 | A1 | 4/2003 | Iwai et al. |
| 2004/0115159 | A1* | 6/2004 | Tadlock ................. A61Q 17/04 424/70.22 |
| 2005/0025957 | A1 | 2/2005 | Issberner et al. |
| 2007/0065390 | A1 | 3/2007 | Spengler et al. |
| 2008/0241204 | A1 | 10/2008 | Leikauf |
| 2009/0068255 | A1* | 3/2009 | Yu ........................ A61Q 19/005 424/450 |
| 2011/0008305 | A1 | 1/2011 | Yu et al. |
| 2014/0113852 | A1 | 4/2014 | Martinus et al. |
| 2017/0087064 | A1 | 3/2017 | Ikeda et al. |

FOREIGN PATENT DOCUMENTS

| CA | 2442660 | 10/2002 |
| CN | 101360481 | 2/2009 |
| CN | 103505382 | 1/2014 |
| CN | 105407860 | 3/2016 |
| EP | 0575461 | 12/1993 |
| EP | 105287235 | 2/2016 |
| EP | 3322399 | 10/2018 |
| KR | 20110072022 | 6/2011 |
| KR | 20140066362 | 6/2014 |
| KR | 101419602 | 7/2014 |
| WO | WO9844896 | 10/1998 |
| WO | WO02080864 | 10/2002 |
| WO | WO2015014604 | 2/2015 |

OTHER PUBLICATIONS

ICSC, "Petrolatum-white", Jun. 2002, download from www.inchem.org/documents/icsc/icsc/eics1440.htm on Aug. 4, 2021. (Year: 2002).*
IPRP2 in PCTEP2017057976; dated Apr. 5, 2018.
Search Report and Written Opinion in PCTEP2017057976; dated Jun. 14, 2017.
Search Report & Written Opinion in EP16166487; dated Aug. 31, 2016.
IPRP2 in PCTEP2017057987; Apr. 5, 2018.
Search Report and Written Opinion in EP16166488; dated Aug. 31, 2016.
Search Report and Written Opinion in PCTEP2017057987; dated Jun. 13, 2017.
Search Report and Written Opinion in PCTEP2017057963; dated Jun. 21, 2017.

(Continued)

*Primary Examiner* — Jianfeng Song

(74) *Attorney, Agent, or Firm* — Krista A. Kostiew

(57) ABSTRACT

The present invention relates to novel oil-in-water nanoemulsions. The oil phase contains oil selected from the group consisting of triglyceride oil and/or petrolatum as well as $C_8$ to $C_{18}$ fatty acid; and the aqueous phase contains specific N-acyl derivatives of amino acid salt as emulsifier.

12 Claims, No Drawings

(56) References Cited

OTHER PUBLICATIONS

Search Report and Written Opinion in EP16166486; dated Nov. 15, 2016.
Cheol Heon Lee et al.; Effect of surfactant mixtures on irritant contact dermatitis potential in man: sodium lauroyl glutamate and sodium lauryl sulphate; Contact Dermatitis; Apr. 1994; pp. 205-209; vol. 30 No 4.
Co-pending U.S. Appl. No. 16/094,077.
Co-pending U.S. Appl. No. 16/094,069.
IPRP1 in PCTEP2017057963; Oct. 23, 2018.
Partial Search Report in EP16166486; dated Aug. 1, 2016.

\* cited by examiner

NANOEMULSIONS COMPRISING FATTY ACID AND N-ACYL DERIVATIVES OF AMINO ACID SALT

CROSS REFERENCE TO RELATED APPLICATIONS

The present application is a U.S. National Phase Application under 35 U.S.C. § 371 of International Application No. PCT/EP2017/057976, filed on Apr. 4, 2017, which claims priority to European Patent Application No. 16166487.5, filed on Apr. 12, 2016, the contents of which are incorporated herein in their entireties.

FIELD OF THE INVENTION

The present invention relates to novel oil-in-water (o/w) nanoemulsions. The nanoemulsions contain (1) an internal oil phase having triglyceride oils and/or petrolatum and $C_8$ to $C_{18}$ fatty acid; and (2) an external aqueous phase containing surfactants which are salts of N-acyl derivatives of dicarboxylic amino acids (e.g., aspartic acid, glutamic acid), salts of N-acyl derivatives of monocarboxylic acids (e.g., glycine, alanine), or mixtures of such derivatives of mono and dicarboxylic amino acids.

The invention is concerned with the provision of such triglyceride oils and petrolatum (benefit agents delivered from nanoemulsion) in small droplets (e.g., 400 nanometers or less), which are more aesthetically pleasing than compositions in which benefit agents are delivered in the form of larger oil droplets. The nanoemulsions further provides high deposition of the triglyceride oil and/or petrolatum when being incorporated in personal cleansing compositions. Further, surprisingly, excellent lather performance of personal cleansing compositions is found when these benefit agents are present in the form of droplets of 400 nanometers or less. Typically, the triglyceride oil and petrolatum benefit agents tend to depress lather speed and volume when in the form of droplets of a few microns.

N-acyl derivatives of both dicarboxylic and monocarboxylic amino acid surfactants of the invention are exceptionally mild surfactants which form the novel nanoemulsions, and which, when the nanoemulsions are incorporated into fully formulated personal liquid cleaners, do not interrupt formation of micellar and/or lamellar structured liquids, nor do they suppress lather. Nanoemulsions using only N-acyl derivatives of dicarboxylic amino acid surfactants as emulsifier are claimed in a co-pending application, where (1) petrolatum jelly yields much larger droplet size than triglyceride oils do under the similar processing conditions, and requires multiple passes at a process pressure of 5,000 psi to achieve a droplet size less than 200 nanometers, depending on specific types of petrolatum jelly; and (2) the dicarboxylic amino acid based surfactants that are in powder format of high purity are more expensive and difficult to handle. Applicants have now found that use of fatty acid as co-emulsifier provides several unexpected advantages. First, it permits the use of less expensive, easier to handle N-acyl derivatives of amino acid surfactants (both mono and dicarboxylic amino acid surfactants) which are in liquid form and contain a high level of inorganic salt. Also nanoemulsions of much smaller droplet size can be prepared more efficiently (e.g., lower process pressure and/or fewer passes through a homogenizer). Further, using fatty acid co-emulsifier permits formation of the small-volume average droplets of our invention (20 to 400 nm) using, as indicated, not just derivatives of dicarboxylic amino acid, but also derivatives of mono carboxylic amino acids. In the absence of fatty acid emulsifier, the volume average of the droplets of petrolatum (using liquid salt of N-acyl derivatives of monocarboxylic amino acids as emulsifier) is well above 400 nanometers.

Specifically, the co-emulsifier (subject of the invention), allows preparation of particularly smaller petrolatum droplets (e.g., 300 nm and below, preferably 250 nm and below, more preferably 200 nm and below) in an efficient manner and further permits use of liquid salts of N-acyl derivatives of both di- and mono-carboxylic amino acids.

BACKGROUND OF THE INVENTION

Skin moisturizing oils (including triglyceride oils and petrolatum benefit agents noted above) are often delivered from personal cleansing compositions (e.g., shower gels, facial and hand cleansers designed to cleanse and moisturize skin) in the form of large oil drops (e.g., 50 to 200 microns or greater).

U.S. Pat. Nos. 5,584,293 and 6,066,608, both to Glenn, Jr., for example, disclose a moisturizing liquid personal cleansing emulsion with at least 10% lipophilic skin moisturizing agent droplets having a diameter of greater than 200 microns.

U.S. Pat. No. 8,772,212 to Restrepo et al. discloses an isotropic cleansing composition containing high level of petrolatum; greater than 50% by volume of the petrolatum particles have a diameter greater than 50, 100, 150 or 200 microns.

Compositions containing large oil drops need to be well structured so they can suspend the large droplets (using, for example, stabilizers). U.S. Pat. Nos. 5,854,293 and 6,066,608, for example, utilize stabilizers selected from crystalline, hydroxyl-containing stabilizers, polymeric thickeners, C10-C18 diesters, amorphous silica or smectite clay. Special blending processes are typically needed to prepare such compositions. For example, compositions must be prepared under low shear to prevent oil droplet size reduction (see U.S. Pat. No. 8,772,212). Although they provide enhanced delivery of benefit agents, these products are generally considered to be less aesthetically appealing to the consumer due to the presence of large oil droplets.

Another method of enhancing the delivery of a benefit agent (e.g., silicone) to the skin, for example, is through the use of cationic hydrophilic polymers such as, for example, hydroxypropyltrimethylammonium derivative of guar gum, sold under the name JAGUAR® C-13-S (see U.S. Pat. No. 5,500,152 to Helliwell). In this reference, silicone oil is a preformed emulsion with oil droplet size ranging from 0.1-1 micron (μm), with a mean particle size of 0.4 μm (there is no mention whether this refers to number average or volume average diameter of droplets). This kind of product tends to be smooth and aesthetically appealing. However, nourishing vegetable oils (triglyceride oils) and highly occlusive skin protectants, such as petrolatum, are typically preferred moisturizers from a cleansing composition.

One challenge facing cleansing compositions that are rich in moisturizing oils is that large amount of oils tend to depress the lather speed and volume.

It is therefore desirable to prepare a personal cleansing composition consisting of triglyceride oils and/or petrolatum nanoemulsion, which is aesthetically appealing, high in deposition of these moisturizing oils, and which maintains high lather performance.

In the subject invention, applicants provide novel nanoemulsions for delivery of triglyceride oils and petrolatum as small (20 to 400 nanometers, particularly 20 to 250, more particularly 20 to 200) volume average diameter droplets. Further, unexpectedly, high lather performance is maintained.

In a co-pending application, applicants claim similar nanoemulsions comprising the salts of N-acyl derivatives of di-carboxylic amino acid (e.g., glutamic acid). In this application, using specific co-emulsifiers, unexpectedly applicants have found they can create nanoemulsions using liquid forms of both di- and mono-carboxylic amino acid based surfactants. These high pH and high salt liquids are cheaper and easier to handle than the powder surfactants applicants were previously using, but are poor emulsifiers if not combined with fatty acid. Further, all other factors being equal, the co-emulsifier permits formation of nanoemulsion with far smaller droplets, and/or using fewer homogenizer passes or lower pressure. Even further, applicants have found that they can form small droplet emulsions when using N-acyl derivatives of mono-carboxylic amino acid as well (e.g., glycine).

Nanoemulsion of the invention comprise (1) an oil phase containing benefit agent droplets selected from the group consisting of triglyceride oils, petrolatum and mixtures thereof; and $C_8$ to $C_{18}$ fatty acid co-emulsifier and (2) an aqueous phase comprising one or more surfactants (primary emulsifier) which are salts of N-acyl derivatives of dicarboxylic amino acid, salts of N-acyl derivatives of monocarboxylic acids or mixtures of such salts; specifically, these surfactants may be selected from (a) acylglutamate salt, acylaspartate salt, acylglycinate salt, acylalaninate salt, with defined N-acyl groups, or (b) mixtures of any of these salts.

The specific N-acyl derivatives of amino acids (aspartic acid, glutamic acid, glycine and alanine) typically comprise 50% or greater, preferably 60% or greater, more preferably 70% or greater of all surfactants present in the aqueous phase of the nanoemulson composition. The salts of N-acyl derivatives of amino acid (any one alone or collectively) are present in an amount greater than any other surfactant present in the aqueous phase.

Both U.S. Pat. Nos. 8,834,903 and 6,541,018 to Simonnet et al. disclose nanoemulsion compositions in which acylglutamate is mentioned as possible surfactant (e.g., U.S. Pat. No. 8,834,903 at column 4, lines 27-31). However, it is disclosed as one of many possible surfactants and, if used, the amino acid based surfactants are used as "additional" components, e.g., as co-surfactant (column 4, line 53). In the examples, the glutamate is never used at levels greater than 0.5% (10% by wt. of total surfactant). The exemplified glutamate is also a salt of N-stearoyl-glutamic acid. This has 018 chain length and provides poor lather in a cleansing application. There is no specific disclosure of acylglutamate comprising 50% or more of surfactant in aqueous phase and fatty acid as co-emulsifier as in our invention.

In U.S. Pat. No. 6,541,018, the internal phase oils are primarily lower molecular weight ester oils (MW less than 400). The lower MW ester oil impacts viscosity and lather of cleansing compositions. The triglycerides of our invention and the petrolatum (having melting point from 30° to 60° C.) of our invention help maintain good viscosity and foam.

It is further noted that nanoemulsions disclosed in U.S. Pat. Nos. 8,834,903 and 6,541,018 have an internal phase where concentration of oil is no higher than 40% of the emulsion. While the concentration of oils of the subject invention may range from 40% to 75% by wt. of total nanoemulsion, preferred ranges are 41 to 70%, preferably 50% to 65%. The higher internal phase is beneficial not only because it consumes less energy to prepare nanoemulsions of smaller droplets, but it also improves the yield of nano oil droplets.

It is also noted that, when the size of oil globules is defined in the Simonnet patents (see column 2, line 64 of U.S. Pat. No. 8,834,903), it is defined by number average. Since number average is the simple averaging of size of all particles (e.g., 1 µm droplet plus 99 µm droplet average to about 50 µm) they do not account for volume average diameter of droplet (e.g., volume average diameter of 1 µdroplet and 99p droplet is much closer to 99 µm). Thus, it is not clear that these references disclose the same low volume average drops as disclosed in our invention.

US2003/0012759 A1 to Bowen-Leaver teaches preparation of nanoemulsion using high pressure devices at about 10, 000 to 20, 000 psi and with multiple passes ([0021] on page 3). It discloses an emulsifier system consisting of anionic surfactant (sodium stearoyl glutamate), non-ionic surfactants (glyceryl stearate/PEG-100 stearate) and stearic acid in Example 1. Fatty acid is used with glyceryl stearate/PEG-100 stearate as co-emulsifiers in oil phase. There is no mention of criticality of combining acyl glutamate (anionic surfactant) and fatty acid as emulsifiers to improve production efficiency of nanoemulsion. In our application, non-ionic emulsifiers, such as glyceryl stearate and PEG-100 stearate, are not included in the emulsifier system for preparing nanoemulsions. The combination of acyl glutamate and fatty acid has been found to unexpectedly reduce petrolatum nanoemulsion droplet size to below 200 nm after only one pass and at 5,000 psi or less, without any other non-ionic surfactants present. Such process efficiency, based on use of fatty acid, is completely unpredictable.

WO 02/080864 A1 discloses oil-in-water nanoemulsions comprising as its principle emulsifiers a ternary system of surfactants comprising a cationic, anionic and bridging surfactant (lines 16-17, page 2). The nanoemulsion is prepared via a high pressure microfluidizer at 10,000 to 20, 000 psi with at least two passes (lines 14-17, page 3)). Acyl glutamate is one of the preferred anionic surfactants and fatty acid is optionally included in the surfactant blend of six surfactants in example 2 (lines 20~21). No mention is made of specific advantages due to addition of fatty acid. The oil level in the nanoemulsion is less than 30% while the oil level in our application is 40% and above.

US2003/0077299 A1 discloses an o/w nanoemulsion comprising an ionic surfactant, a water phase and an oil phase which either comprises a ceramide or fatty acid. N-acylglutamate salts are one of many examples of anionic surfactants (lines 15~17 in on page 1). In Example 1 emulsion (6), nanoemulsion containing 16.4% silicone oil is prepared at a pressure of 2,800 kg/cm2 (~40,000 psi) with three passes ([0060] on page 4), using an emulsifier system consisting of fatty acids (palmitic acid and stearic acid) and acyglutamate. The oil level is far below 40-75%, the ratio of fatty acid/acyl glutamate (2) is much higher than specified in our application. The criticality of combing high oil level (e.g. 40% and above) and fatty acid/amino acid ratio is not appreciated in reducing the processing energy in preparing nanoemulsions, especially when petrolatum Jelly is concerned.

The unique nanoemulsions of the present invention contain small oil droplets (400 nanometers or less) which are aesthetically pleasing, efficiently deliver the benefit agent triglycerides oils or petrolatum, and maintain excellent lather when being incorporated into personal cleansing compositions. Further, the specific surfactants used, including the chain length of N-acyl chain, provide excellent, "mild" cleansing and ensure foam maintenance when the nanoemulsons are used in personal cleansing products.

With regard to mildness of surfactant, applicants note "Effect of surfactant mixtures on irritant contact dermatitis potential in man: sodium lauroyl glutamate and sodium lauryl sulphate" by C. H. Lee et al (Contact Dermatitis, Volume 30, Issue 4, pages 205-209, April 1994); and Schmucker et al., U.S. Patent Publication No. 2002/0054861 A1, wherein it is disclosed that sodium lauroyl glutamate and sodium cocyl glutamate, for example, are mild surfactants and their utilization can decrease irritation potential in sodium lauryl sulphate and SLES.

BRIEF DESCRIPTION OF THE INVENTION

Specifically, the present invention relates to nanoemulsion compositions comprising:
a) an internal oil phase comprising (i) 40 to 75% by wt. of total nanoemulsion of oil selected from the group consisting of triglyceride oil, petrolatum and mixtures thereof, wherein the melting point of the petrolatum is 30 to 60° C.; and (ii) 0.5 to 10% by wt. nanoemulsion of a $C_8$ to $C_{18}$, preferably $C_{10}$ to $C_{14}$ fatty acid (e.g., $C_{12}$ lauric acid), and
b) an external aqueous phase comprising 1.6 to 15% by wt. (as active) of total nanoemulsion of a surfactant or surfactants which are the salts of N-acyl derivatives of amino acid and, preferably, said surfactant or surfactants is selected from the group consisting of
(i) salt of N-acyl derivatives of di-carboxylic amino acid (e.g., acylglutamate acid or acylaspartate), wherein greater than 65% (e.g., 65 to 100%, preferably 65 to 90%) of the acyl group has chain length of $C_{14}$ or less;
(ii) salt of N-acyl derivatives of mono-carboxylic acid (e.g., acylglycinate, acylalanate), wherein greater than 65% of the acyl group (e.g., 65 to 100%, preferably 65 to 90%) has chain length $C_{14}$ or less; and
(iii) mixtures thereof;
wherein the surfactant of (b) comprises 50% or greater, preferably 60% or greater, preferably 70% or greater, preferably 75 to 100% of all surfactants present in the aqueous phase of the nanoemulsion;
wherein the volume average diameter of the oil droplets of (a) is 20 to 400 nanometers.

It should be understood that the claims are directed to the composition. That is, the claim is intended to cover the salts of N-acyl derivatives of amino acids, for example, whether formed by us or bought as a prepared surfactant product (as would occur in the vast majority of all cases).

Using fatty acid as co-emulsifier, nanoemulsions of the invention will typically have volume average diameter of droplets of 350 or less, or 20 to 300; or 20 to 250; or 20 to 200.

The nanoemulsions are typically prepared by mixing the oil phase and the aqueous phase using a conventional rotor/stator or other type of high shear devices and further processed via homogenizer at a process pressure of 7000 pounds per square inch (psi) or less, preferably 6000 psi or less; most preferably 5000 psi or less. Using the same components, but no $C_8$ to $C_{18}$ fatty acid as co-emulsifier in the oil phase, at the same pressure the droplet size will be typically higher than if fatty acid is used.

Because greater than 65% of chain length of N-acyl chains on the amino acid based surfactants are $C_{14}$ or less, the nanoemulsion composition, once formed, provides several advantages. For example, the nanoemulsion composition can be readily incorporated into personal cleanser liquids which are structured by micelles or are lamellar structured. Further, the predominantly shorter chain N-acyl groups (relative to longer chain C16 and C18, for example) on the surfactant enable good lather formation in the cleanser liquids.

Thus, the novel nanoemulsions are sensorially pleasing (due to small droplet size), provide efficient oil deposition, provide superior stability (again because of smaller droplet size), and are ideally suited (because of chain length selection) for use in personal cleansing liquids while providing excellent lather.

In another aspect, the invention relates to process for preparing an emulsion comprising:
a. an internal oil phase comprising (i) 40 to 75% by wt. of total nanoemulsion of oil selected from the group consisting of triglyceride oil, petrolatum and mixtures thereof, wherein the melting point of the petrolatum is 30 to 60° C.; and (ii) 0.5 to 10% by wt. nanoemulsion of a $C_8$ to $C_{18}$, preferably $C_{10}$ to $C_{14}$ fatty acid (e.g., 012 lauric acid), and
b. an external aqueous phase comprising 1.6 to 15% by wt. (as active) of total nanoemulsion of a surfactant or surfactants which are the salts of N-acyl derivatives of amino acid and, preferably, said surfactant or surfactants is selected from the group consisting of
i. salt of N-acyl derivatives of di-carboxylic amino acid (e.g., acylglutamate acid or acylaspartate), wherein greater than 65% (e.g., 65 to 100%, preferably 65 to 90%) of the acyl group has chain length of $C_{14}$ or less;
ii. salt of N-acyl derivatives of mono-carboxylic acid (e.g., acylglycinate, acylalanate), wherein greater than 65% of the acyl group (e.g., 65 to 100%, preferably 65 to 90%) has chain length $C_{14}$ or less; and
iii. mixtures thereof;
wherein the surfactant of (b) comprises 50% or greater, preferably 60% or greater, preferably 70% or greater, preferably 75 to 100% of all surfactants present in the aqueous phase of the nanoemulsion;
wherein the volume average diameter of the oil droplets of (a) is 20 to 400 nanometers
wherein said process comprises:
1) heating aqueous phase to 55 to 75° C.;
2) heating oil phase to 55 to 75° C. or until molten;
3) adding oil phase to aqueous phase and mixing to form coarse emulsions in a rotor stator high shear device at 1000 to 6000 revolution per minute (rpm); or using a homogenizer at pressure of 200 to 500 pounds per square inch (psi);
4) pumping the coarse emulsion once or multiple times through homogenizer at process pressure of 7000 psi or less, preferably 6000 psi or less, preferably 5000 psi or less; and
5) cooling emulsion to room temperature.

In step 3), alternatively, the coarse emulsion may be formed using a homogenizer operating at pressure of 200 to 500 psi.

DETAILED DESCRIPTION OF THE INVENTION

Except in the examples, or where otherwise explicitly indicated, all numbers in this description indicating amounts of material or conditions of reaction, physical properties of materials and/or use are to be understood as modified by the word "about." All amounts are by weight of the final composition, unless otherwise specified.

It should be noted that in specifying any range of concentration or amount, any particular upper concentration can be associated with any particular lower concentration or amount.

For the avoidance of doubt, the word "comprising" is intended to mean "including" but not necessarily "consisting of" or "composed of." In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

The present invention provides novel nanoemulsions containing a specific selection of oils and surfactants. The nanoemulsions can be prepared using processing pressure of 7000 psi or less. The novel nanoemulsions are ideally suited for use in liquid cleansing compositions, for example, structured (e.g., micellar or lamellar structured) liquid cleansing compositions.

Specifically, the N-acyl derivatives of amino acid surfactants (e.g., acylglutamate, acylaspartate, acylglycinate, acylalanate surfactants) have greater than 65%, preferably greater than 75%, preferably greater than 80% of $C_{14}$ or less acyl chain (preferably they have greater than 75% acyl chain which are $C_{12}$, $C_{14}$ and mixtures thereof). The chosen surfactants provide multiple advantages when final nanoemulsions are mixed into fully formulated liquid personal cleansing compositions. First, the amino acid surfactants are known to be less irritating than harsher surfactants typically used such as sodium lauryl sulphate and sodium lauryl ether sulphate (SLES). Also, as noted, the chain length is selected so the surfactants are suitable for use in structured personal cleansing liquids while providing minimal interference with such structuring. Further, the selected predominantly shorter chain lengths ensure the surfactants will provide good foam.

In a co-pending application, applicants claim similar nanoemulsions which comprise N-acyl derivatives of di-carboxylic acids and which are not specifically directed to those containing fatty acid emulsifier. Small size droplets are obtained. In this application, unexpectedly we have found that using fatty acid as co-emulsifier yields significantly smaller droplets, and these small droplet nanoemulsions are obtained more efficiently.

Furthermore, using fatty acid as co-emulsifier permits use of N-acyl derivatives of amino acid surfactants which are in liquid format, containing high amount of inorganic salts and with pH as high as 10 (which were not used in co-pending cases). Surprisingly, the co-emulsifier permits production of small droplets whether the amino acid surfactants are derivatives of dicarboxylic or mono-carboxylic amino acids. Small droplet size and efficient processing is function of specific combination of specific surfactants (e.g., anionic) and specifically fatty acid. Higher amounts of fatty acid used with glutamate, for example, are more efficient (form smaller drops) than using more total surfactant, but lesser fatty acid. That is, a unique synergy between surfactants of the invention and fatty acid and, as noted, works particularly well with oils (e.g. petrolatum jelly) of the invention.

In short, significantly smaller droplets are obtained (using fatty acids) when using the same materials, and these small droplet nanoemulsions are obtained more efficiently. In general, small volume average size droplets help provide more efficient deposition. For example, cationic polymers typically used in fully formulated liquid cleanser more readily deposit the smaller droplets than larger droplets. Large oil droplets also require stabilizers to suspend the large oil droplets. The small size oil droplets from the nanoemulsion, when incorporated into a cleansing liquid, also provide greater stability. Small droplets are also viewed as more aesthetically pleasing.

The nanoemulsions of the invention are defined with more particularity below.

Oil Phase

Oils in the oil phase of the nanoemulsions may be triglyceride oil or oils (animal and/or vegetable oils); petrolatum; or mixtures of one or more triglyceride oil with petrolatum. Petrolatum is particularly preferred.

Examples of triglyceride oils which may be used include soybean oil, sunflower seed oil, coconut oil, rapeseed oil, palm oil, palm kernel oil, grape seed oil and fish oil. Soybean and sunflower seed oils are preferred triglycerides.

The oil in the oil phase may also be petrolatum. The petrolatum preferably has a melting point ranging from 30° to about 60° C. Examples of such petrolatum oils include Vaseline® Petrolatum Jelly from Unilever, White Petrolatum USP from Calumet Penreco, Petrolatum G2212 and White Protopet® 1S from Sonneborn.

The oils can range from 40% to 75% by wt., preferably 41% to 65% by wt. of the total nanoemulsion composition. The preferred volume average diameter of the triglyceride oil or petrolatum droplets is 20 to 400 nm, preferably 20 to 300 nm, more preferably 20 to 250 nm, or 20 to 200 nm. Lower level can be 20 or 30 or 40 or 50; upper level can be 300 or 250 or 200 or 175 or 150.

The choice of triglyceride oils and petrolatum helps impart emolliency and occlusivity to skin when the triglyceride oils and/or petrolatum deposit onto skin after the skin is washed with fully formulated cleansing compositions into which the nanoemulsions of this invention have been incorporated.

In addition to the triglyceride oil (or oils) and/or petrolatum, the oil phase may comprise oil soluble skin beneficial actives such as, for example, Vitamin A, Vitamin E, sun screen, fragrances, retinol palmitate, 12-hydroxy stearic acid, conjugated linoleic acid; antibaterial agents; mosquito repellents etc. at level of 0.01 to 5%.

Another ingredient which might be found in the oil phase is an oil phase stabilizer. For example, small amounts (0.01 to 2%, preferably 0.1-1% by wt. nanoemulsion) of antioxidant may be used. When the oil used is triglyceride, a preferred antioxidant which may be used is butylated hydroxytoluene (BHT). This is often used as a food grade antioxidant.

In addition to oils, the oil phase contains $C_8$ to $C_{18}$, preferably $C_{10}$ to $C_{14}$ fatty acids in an amount ranging from 0.5 to 10% by wt. total nanoemulsion. Examples of fatty acid which may be used include lauric acid, myristic acid, coconut fatty acid and mixtures thereof. The fatty acid is used as a co-emulsifier. For example, the oil phase may contain petrolatum ranging from 40 to 70% by wt, preferably 41 to 65% by wt. of nanoemulsion and lauric acid ranging from 0.5 to 8% by wt. of nanoemulsion.

Aqueous Phase

The aqueous phase contain salts of N-acyl derivatives of amino acids (e.g., di- or mono-carboxylic acid) as emulsifier (50% or greater, preferably 60% or greater of all surfactant present in the aqueous phase). Preferred di-carboxylic amino acid emulsifiers are acylglutamate and acylaspartate surfactants. Preferred mono-carboxylic amino acid emulsifiers are acylglycinate and acylalanate. Preferably, these are potassium and/or sodium salts of N-acyl derivatives of amino acids, wherein greater than 65% of the acyl chains has chain length $C_{14}$ or less, e.g., $C_8$ to $C_{14}$ (e.g., derived from coconut fatty acid). The acyl chains preferably have greater than 75%, more preferably greater than 80% $C_{14}$ or less chain length. Preferably, greater than 75%, most preferably greater than 80% of the chain length are $C_{12}$, $C_{14}$ or mixtures thereof. These predominantly short chain acyl groups (relative to longer chain $C_{16}$ and $C_{18}$, for example) ensure that, when nanoemulsions of the invention are incorporated into fully formulated liquid cleansing compositions (especially structured liquid cleansing compositions), they help maintain or enhance foaming capacity.

There are typically two formats of amino acid surfactants commercially available. One is powder or flake format, which is typically more expensive and high in purity. Examples of solid dicarboxylic amino acid surfactants include:

sodium N-cocoyl-L-glutamate (e.g., Amisoft® CS-11 by Ajinomoto)
sodium N-lauroyl-L-glutamate (e.g., Amisoft® LS-11 by Ajinomoto)
sodium N-myristoyl-L-glutamate (Amisoft® MS-11 by Ajinomoto)
potassium N-cocoyl_I-Glutamate (e.g., Amisoft® CK-11 by Ajinomoto)
potassium N-myristoyl-L-glutamate (Amisoft® MK-11 by Ajinomoto)
potassium N-lauroyl-L-glutamate (Amisoft® LK-11 by Ajinomoto)
Sodium Lauroyl Aspartate (AminoFoamer™ FLMS-P1 by Asahi Kasei Chemical Corporation)
Sodium Lauroyl Glutamate (Aminosurfact™ ALMS-P1/S1 by Asahi Kasei Chemical Corporation)
Sodium Myristoyl Glutamate (Aminosurfact™ AMMS-P1/S1 by Asahi Kasei Chemical Corporation)

Examples of solid monocarboxylic amino acids surfactants include:

sodium cocoyl glycinate (e.g., Amilite® GCS-11 by Ajinomoto)
potassium cocoyl glycinate (e.g., Amilite® GCK-11 by Ajinomoto One of unexpected discoveries of this invention is that, in addition to amino acids noted above (which are in powder form and are not convenient to handle in plant production), using fatty acid as co-emulsifier permits use of amino acid surfactants in liquid form, which is typically less expensive but high in pH and inorganic salt As noted in the comparative examples, in the absence of the fatty acid emulsifier, applicants could not form a coarse emulsion or droplet size was very high (much greater than 400 nm); using acylglutamate, for example, the coarse emulsion phase separated and/or, when using liquid acylglutamate with high level of citric acid to lower the pH, droplet size was about 2.5 times as large as when fatty acid is used. In the case of acylglycinate, for example, without fatty acid the droplet size was 14 times larger compared to when fatty acid was present. The addition of a fatty acid, especially lauric acid, to the industrial liquid amino acid surfactant as a co-emulsifier resulted in the formation of stable coarse emulsions and the efficient formation of smaller oil droplets to form a highly superior nanoemulsion. For example, it was possible to produce petrolatum oil droplet sizes below 200 nm with only one pass through the homogenizer at 5000 psi (see Example 6).

Liquid amino acid surfactants typically contains 20-35% surfactant active, high in pH and inorganic salt (e.g. from 3 to 6% NaCl). Examples include:

AMISOFT® ECS-22SB: Disodium Cocoyl Glutamate (30% Aqueous Solution)
AMISOFT® CS-22: Disodium Cocoyl Glutamate and sodium Cocoyl Glutamate (25% Aqueous Solution)
AMISOFT® CK-22: Potassium Cocoyl Glutamate (30% Aqueous Solution)
AMISOFT® LT-12: TEA-Lauroyl Glutamate (30% Aqueous Solution)
AMISOFT® CT-12 TEA-Cocoyl Glutamate (30% Aqueous Solution)
AMILITE® ACT-12: TEA-Cocoyl Alaninate (30% Aqueous Solution)
AMILITE® ACS-12: Sodium Cocoyl Alaninate (30% Aqueous Solution)
AMILITE® GCK-12/GCK-12K: Potassium Cocoyl Glycinate (30% Aqueous Solution)
Aminosurfact™ ACDS-L: Sodium Cocoyl Glutamate (25% Aqueous Solution)
Aminosurfact™ ACDP-L: Potassium Cocoyl Glutamate (22%)+Sodium Cocoyl Glutamate (7%)
Aminosurfact™ ACMT-L: TEA-Cocoyl Glutamate (30% Aqueous Solution)
AminoFoamer™ FLDS-L: Sodium Lauroyl Aspartate (25% Aqueous Solution)

In addition to the Amisoft® and Amilite® series from Ajinomoto, Aminosurfact™ and AminoFoamer™ from Asahi Kasei Chemical Corporation, other suppliers of liquid amino acid surfactants include Clariant (e.g. Hostapon SG Sodium cocoyl glycinate), Solvay (e.g. Gerapon® PCG Potassium Cocoyl Glutamate aqueous solution; Gerapon® LG 3S sodium lauryl glycinate with glycerin), Galaxy (Galsoft® KCGL Potassium Cocoyl Glutamate aqueous solution; GalSoft® SCG plus sodium cocoyl glycinate, 20% active) and Sino Lion (Eversoft® USK-30K Potassium Cocoyl Glutamate aqueous solution; Eversoft® YCS-30S sodium cocoyl glycinate).

Additionally, other mild ionic cleansing surfactants can be used in the aqueous phase. Anionic surfactants which may be used include sodium cocoyl isethionate, sodium cocoyl methyl isethionate, sodium lauroyl isethionate, sodium methyl cocoyl taurate and other amino acid based surfactants, such as sodium lauroyl sarcosinate, sodium cocoyl sarcosinate. Amphoterics such as coco betaine, cocamidopropyl betaine, sodium lauroamphoacetate, Lauramidopropyl hydroxysultaine and Cocamidopropyl hydroxysultaine can also be used. These co-surfactants are typically present at a level of less than 50%, preferably less than 40%, more preferably less than 30% of total surfactants in the aqueous phase.

Overall surfactants in aqueous phase comprise 1.6 to 15% preferably 4 to 12% by wt. of total nanoemulsion. As indicated, the salts of N-acyl derivatives of amino acid, preferably acylglutamate, acylaspartate, acylglycinate, acylalaninate or mixtures thereof are the principal surfactant of the nanoemulsion. They constitute 50% or greater, preferably 60% or greater of all surfactant in the aqueous phase. Preferably they constitute greater than 70%, more preferably greater than 75%. They may of course be the only surfactant present in the aqueous phase.

Preferably, the aqueous phase may contain a preservative or preservatives. Typically, they are present at a level of 0.01 to 1.0%, preferably 0.1 to 0.5% by wt.

Nanoemulsions of the invention, have volume average diameter (also used interchangeably in and with terms "volume mean diameter" or "volume average size") of 400 nm or less, preferably 20 nm to 300 nm, more preferably 20 to 250 nm, more preferably 20 to 200 nm.

Nanoemulsions with droplet sizes of these ranges are obtained in the subject invention using relatively low pressure applied by a high pressure homogenizer or a high pressure sonolator. Pressures used are 7000 psi or less, preferably 6000 psi or less, most preferably 5000 psi or less.

Preparation of Nanoemulsion

Nanoemulsions are typically formed in a two stage process.

The first mixing stage is used to form a coarse emulsion. The oil phase and aqueous phase were heated up to 75° C. (55° to 75° C.) separately such that each phase was clear and uniform (oil phase heated to 55 to 75° C. or until molten); then the oil phase was mixed with the aqueous phase with intensive mixing. Intensive mixing can be accomplished via conventional means including mixing the materials in a stirred tank and passing the mixture through a rotor/stator mixer such as the Silverson® high shear in-line mixer or mixing them in the vessel with a high shear mixer such as the Scott® Turbon mixer. Alternatively, the coarse emulsion may be created by using a continuous high shear mixing device such as the standard Sonolator device produced by Sonic Corporation of Connecticut. These standard sonolators are normally operated at pressures of 200-500 psi to form coarse emulsion.

The second stage of the process is to pass the coarse emulsion through a high pressure homogenizer to form the nano-emulsion. Suitable high pressure homogenizers are the Nano DeBee homogenizer of BEE International (Massachusetts, USA) and the High Pressure Sonolator device also produced by Sonic Corporation of Connecticut, USA. These devices can be operated up to 1000-5000 psi in order to produce nanoemulsions of less than 300 nm. For hydrophobic oils, either petrolatum or triglycerides, only one pass through the Nano DeBEE or high pressure sonolator is required to reach the desired nano-emulsion particle size, when fatty acid is included as co-emulsifier.

In the examples, the following terms are defined as noted below:

Pass #: the number of times the emulsion passes through high pressure homogenizer D[4, 3]: volume average diameter or volume mean diameter or volume average size D[3, 2]: surface area mean diameter The average diameters are determined by a Malvern Mastersizer.

Examples 1-6 and Comparatives A-H

Coarse emulsions were prepared in a one liter ESCO mixer equipped with a rotor/stator high shear device (ESCO-LABOR AG, Switzerland). The aqueous phase was added to the ESCO mixer and heated up to 75° C. or till clear. The oil phase was combined and heated up to 75° C. or till molten in a separate container. The oil phase was gradually added to the aqueous phase in the ESCO mixer under agitation and/or was intensively mixed by the rotor/stator device. When the addition of all oil phased was completed and the coarse emulsion was formed in the ESCO mixer, the coarse emulsion was transferred and passed through High Pressure homogenizer Nano DeBEE one or 2 times to arrive at the desired droplet size at a process pressure of 5000 psi.

Examples 1-2 and Comparatives A-C

In Examples 1-2 and Comparatives A-C, liquid potassium cocoyl glutamate (27.2% active) high in pH (about 10) and high in inorganic salt (about 3 to 6% KCl) was used as primary emulsifier. Coarse emulsions that are stable enough were passed through the Nano DeBEE once at a process pressure of 5000 psi to form nanoemulsions. The oil droplet size was measured using Malvern Mastersizer afterwards.

| Ingredient | Example 1 Wt. % | Example 2 Wt % | Comparative A Wt. % | Comparative B Wt. % | Comparative C Wt. % |
| --- | --- | --- | --- | --- | --- |
| Oil Phase | | | | | |
| White petrolatum USP | 50% | 50% | 50% | 50% | 50% |
| Lauric acid | 4% | 2% | | | |
| Aqueous Phase | | | | | |
| Potassium Cocoyl Glutamate (Solvay, Active 27.2%) | 27.4% (7.5% active) | 27.4% (7.5% active) | 27.4% (7.5% active) | 27.4% (7.5% active) | 27.4% (7.5% active) |
| Deionized Water | Q.S.* | Q.S.* | Q.S.* | Q.S.* | Q.S.* |
| Citric acid | | 1.28% | | 1.28% | 1.92% |
| DMDM Hydantoin (and) Iodopropynyl Butylcarbamate (Glydant ™ Plus ™ Liquid) | 0.40% | 0.4% | 0.40% | 0.40% | 0.4% |
| Process pressure, PSI | 5000 | 5000 | | Coarse emulsion phase separated in 2 minutes | 5000 |
| $D_{[3,2]}$ nm | 127 | 138 | No coarse emulsion formed | | 187 |
| $D_{[4,3]}$ nm | 186 | 209 | | | 476 |
| pH | 6.76 | 5.71 | 10.0 | 5.57 | 5.22 |

*Amount needed (e.g., to obtain 100% by wt.)

No coarse emulsion was formed in comparative A. When 1.28% citric acid was added to the aqueous phase as shown in Comparative B to lower the pH to the range about 5 to 6, coarse emulsion was formed with intensive mixing but phases quickly separated when the rotor/stator high shear device was stopped. When 1.92% citric acid was added to the aqueous phase as shown in Comparative C, coarse emulsion was formed and stayed uniform long enough to be passed through Nano DeBEE, yielding volume average mean droplet size of 476 nm.

When 2 to 4% Lauric acid was added to the oil phase as shown in Example 1 and 2, stable coarse emulsion formed with or without citric acid. One pass through Nano DeBEE at the same process pressure of 5000 psi, yielding volume average mean droplet size as low as 186 nm. Thus, addition of lauric acid not only diminishes amount of citric acid needed to form coarse emulsion (Example 1), but formed much smaller droplets of 209 or less in only one pass.

Example 3 and Comparative D

In Example 3 and Comparative D, liquid sodium cocoyl glycinate (20% active) high in pH (about 10) and high in inorganic salt (about 3 to 6% NaCl) was used as primary emulsifier. Coarse emulsions that are stable enough were passed via Nano DeBEE once at a process pressure of 5000 psi and the oil droplet size was measured using Malvern Mastersizer afterwards.

| Ingredient | Comparative D wt. % | Example 3 wt % |
|---|---|---|
| Oil Phase | | |
| White petrolatum USP | 50% | 50% |
| Lauric acid | 0% | 4% |
| Aqueous Phase | | |
| Sodium Cocoyl Glycinate (Galsoft, Active 20%) | 40% (8% active) | 40% (8% active) |
| Deionized Water | Q.S. | Q.S. |
| DMDM Hydantoin (and) Iodopropynyl Butylcarbamate (Glydant ™ Plus ™ Liquid) | 0.40% | 0.4% |
| Process pressure, PSI | 5000 | 5000 |
| $D_{[3,2]}$ nm | 1900 | 161 |
| $D_{[4,3]}$ nm | 3917 | 266 |
| pH | 9.1 | 6.59 |

Although a coarse emulsion was formed when passing the composition through Nano DeBEE at 5000 psi once, the oil droplet size was 3917 nm; when lauric acid was added to oil phase, under the same process conditions, oil droplets of 266 nm were obtained. Particle size was thus 14 times smaller when using lauric acid than without using lauric acid.

Examples 4-5 and Comparatives E and F

The oil is soybean oil and the emulsifier is flake form of Potassium cocoyl Glutamate (AMISOFT® CK-11). With or without lauric acid added to oil phase, stable coarse emulsions were formed and passed through Nano DeBEE once either at process pressure of 5000 psi or 3000 psi. The pH of the final nanoemulsions fall between about 5.6 to 5.8. At 5000 psi, with 4% lauric acid added, the volume average droplet was reduced from 188 nm to 143 nm (see Comparative E and Example 4); at 3000 psi, with 4% lauric acid added, the volume average droplet was reduced from 268 nm to 161 nm (see Comparative F and Example 5).

| Ingredient | Comparative E Wt. % | Comparative F wt % | Example 4 Wt. % | Example 5 Wt. % |
|---|---|---|---|---|
| Oil Phase | | | | |
| Soybean Oil | 55% | 55% | 55% | 55% |
| BHT Food Grade Antioxidant | 0.4% | 0.4% | 0.4% | 0.4% |
| Lauric acid | | | 4% | 4% |
| Aqueous Phase | | | | |
| Potassium cocoyl Glutamate (AMISOFT ® CK-11) | 8.8% | 8.8% | 8.8% | 8.8% |
| Deionized Water | Q.S. | Q.S. | Q.S. | Q.S. |
| DMDM Hydantoin (and) Iodopropynyl Butylcarbamate (Glydant ™ Plus ™ Liquid) | 0.40% | 0.4% | 0.40% | 0.40% |
| Process pressure, PSI | 5000 | 3000 | 5000 | 3000 |
| $D_{[3,2]}$ nm | 127 | 163 | 113 | 116 |
| $D_{[4,3]}$ nm | 188 | 268 | 143 | 161 |
| pH | 5.82 | 5.82 | 5.65 | 5.65 |

Example 6 and Comparatives G and H

Stable coarse emulsion was formed using 50% White Petrolatum and Potassium cocoyl Glutamate (AMISOFT® CK-11) as primary emulsifier with or without lauric acid as co-emulsifier. Without lauric acid, the coarse emulsion passed Nano DeBEE once and two times at 5000 psi separately, yielding nanoemulsion with volume average droplet of 374 nm and 283 nm respectively. With 4% lauric acid and only one pass at 5000 psi through Nano DeBEE, the volume average droplet was reduced to 168 nm. Thus, lauric acid greatly improved the efficiency of small drop formation.

| Ingredient | Comparative G Wt. % | Comparative H wt % | Example 6 wt % |
|---|---|---|---|
| Oil Phase | | | |
| White Petrolatum USP | 50% | 50% | 50% |
| Lauric acid | | | 4% |
| Aqueous Phase | | | |
| Potasium cocoyl Glutamate (AMISOFT ® CK-11) | 8% | 8% | 8% |
| Deionized Water | Q.S. | Q.S. | Q.S. |
| DMDM Hydantoin (and) Iodopropynyl Butylcarbamate (Glydant ™ Plus ™ Liquid) | 0.40% | 0.4% | 0.4% |
| Process pressure, PSI | 5000 | 5000 | 5000 |
| Number of Passes | 1 | 2 | 1 |
| $D_{[3,2]}$ nm | 188 | 168 | 120 |
| $D_{[4,3]}$ nm | 374 | 283 | 168 |
| pH | 5.91 | 5.91 | 5.73 |

Examples 7-13

50-55% Petrolatum was used to form nanoemulsions, with potassium cocoyl glutamate (30%) or Sodium Cocoyl Glycinate (20%) in the liquid form as primary emulsifier, ranging 4 to 8.2% in active and lauric acid as co-emulsifier ranging 1 to 4%. The coarse emulsion was prepared by a low pressure sonolator at a pressure up to 450 psi, where the molten oil phase and aqueous phase at 60 to 75 C were simultaneously pumped through the orifice of a low pressure sonolator and thus formed the coarse emulsion. The coarse emulsion was further pumped through a high pressure sonolator only once with a pressure up to 2500 psi to form nanoemulsion. Examples 12 and 13 used different lower pressure in forming coarse emulsion and nanoemulsion as shown in the table.

With 4% lauric acid as co-emulsifier as shown in examples 10, 11 and 12, nanoemulsion with volume average droplet ranging from 144 to 198 nm was formed after one pass of high pressure sonolator at pressure of 2500 psi or less. With 4% lauric acid as co-emulsifier as shown in example 11 and 12, even the coarse emulsion yielded volume average droplet size below 300 nm after passing the low pressure sonolator at 450 psi or less.

Efficient production of small droplets is not believed to be just function of total surfactant amount, but rather of type and interaction of surfactants. This is seen comparing Example 7 to Example 10. Although there is less overall surfactant active in Example 10 (8% vs. 9.2% in Example 7), because of interaction of anionic glutamate and greater amounts of fatty acid, the droplet size for petrolatum of Example 10 is 158 nm versus 316 nm for Example 7.

| Example-> Ingredient | 7 Wt. % | 8 Wt % | 9 Wt. % | 10 Wt. % | 11 Wt. % | 12 Wt. % | 13 Wt. % |
|---|---|---|---|---|---|---|---|
| Oil Phase | | | | | | | |
| Petrolatum G2212 | 55% | 55% | 55% | 55% | 55% | 55% | |
| White petrolatum | | | | | | | 50% |
| Lauric acid | 1% | 2% | 2% | 4% | 4% | 4% | 4% |
| Aqueous Phase | | | | | | | |
| Potassium Cocoyl Glutamate(Galsoft KCGL, Active 30%) | 27.3% (8.2% active) | 27.3% (8.2% active) | 13.3% (4% active) | 13.3% (4% active) | 20% (6% active) | 27.4% (8.2% active) | |
| Sodium Cocoyl Glycinate (Galsoft SCG plus, Active 20%) | | | | | | | 40% (8% active) |
| Deionized Water | Q.S. | Q.S. | Q.S. | Q.S. | Q.S. | Q.S. | Q.S. |
| DMDM Hydantoin (and) Iodopropynyl Butylcarbamate (Glydant™ Plus™ Liquid) | 0.158% | 0.158% | 0.158% | 0.158% | 0.158% | 0.158% | 0.4% |
| $D_{[4,3]}$, nm (coarse emulsion formed @ 450psi) | 855 | 514 | 560 | 350 | 279 | 285 (350 psi) | 334 (350 psi) |
| $D_{[4,3]}$, nm (Nanoemulsion formed @ 2500psi) | 316 | 217 | 286 | 158 | 144 | 198 (1000 psi) | 228 (2000 psi) |
| pH | 8.4 | 7.88 | 7.36 | 7.0 | 7.23 | 7.25 | 6.7 |

The invention claimed is:

1. A nanoemulsion composition comprising:
 a) an internal phase comprising (1) 40 to 75% by wt. of total nanoemulsion composition of an oil phase containing benefit agent droplets comprising oils selected from the group consisting of triglyceride, petrolatum and mixtures thereof, wherein the melting point of the petrolatum is 30 to 60° C.; and (ii) 1 to 10% by wt. nanoemulsion of a co-emulsifier comprising a $C_8$ to $C_{18}$ fatty acid; and
 b) an external aqueous phase comprising 1.6 to 15% by wt. of total nanoemulsion composition of a primary emulsifier comprising a surfactant or surfactants which are N-acyl derivatives of amino acid salt;
 wherein the surfactant of (b) comprises 50% or greater of all surfactants present in said external aqueous phase of the nanoemulsion wherein the salt of N-acyl derivative of dicarboxylic amino acid is a salt of acylglutamic acid, salt of acylaspartic acid or mixture thereof;
 wherein the volume average diameter of droplets of (a) is 20 to 400 nanometers.

2. The nanoemulsion composition according to claim 1, wherein said surfactant or surfactants are selected from the group consisting of
 (i) salt of N-acyl derivatives of dicarboxylic amino acid, wherein greater than 65% of the acyl group has chain length of $C_{14}$ or less; and
 (ii) salt of N-acyl derivatives of monocarboxylic amino acid, wherein greater than 65% of the acyl group has chain length $C_{14}$ or less; and
 (iii) mixtures thereof.

3. The nanoemulsion composition according to claim 1, wherein volume average diameter of the droplets is 20 to 250 nm.

4. The nanoemulsion composition according to claim 1, wherein volume average diameter of droplets is 20 to 200 nm.

5. The nanoemulsion composition according to claim 1, wherein the benefit agent droplets are an oil, wherein the oil is a triglyceride oil and said triglyceride oil is selected from the group consisting of soybean oil, sunflower seed oil, coconut oil, rapeseed oil, palm oil, palm kernel oil, grape seed oil, fish oil and mixtures thereof.

6. The nanoemulsion composition according to claim 1, wherein the oil is petrolatum and the melting point of the petrolatum is 30 to 60° C.

7. The nanoemulsion composition according to claim 1, wherein the oil is an oil mixture comprising triglyceride oil and petrolatum.

8. The nanoemulsion composition according to claim 1, wherein said fatty acid having a chain length $C_8$-$C_{18}$ is selected from the group consisting of lauric acid, myristic acid, coconut fatty acid and mixtures thereof.

9. The nanoemulsion composition according to claim 8, wherein the co-emulsifier is a fatty acid present at a level of 1 to 7% by wt.

10. The nanoemulsion composition according to claim 1, wherein the salts of N-acyl derivatives of the amino acid are mono- and/or di-sodium and/or potassium salts.

11. The nanoemulsion composition according to claim 1, wherein the nanoemulsion is prepared at pressure from a homogenizer or sonolator and said pressure is 7000 psi or below.

12. The nanoemulsion composition according to claim 1, wherein the surfactant of (b), prior to formation of the nanoemulsion, is a powder or liquid surfactant.

* * * * *